(12) United States Patent
Uchiyama et al.

(10) Patent No.: US 10,856,834 B2
(45) Date of Patent: Dec. 8, 2020

(54) RADIATION IMAGING APPARATUS, METHOD OF CONTROLLING RADIATION IMAGING APPARATUS, RADIATION IMAGING SYSTEM, AND NON-TRANSITORY COMPUTER-READABLE STORAGE MEDIUM

(71) Applicant: CANON KABUSHIKI KAISHA, Tokyo (JP)

(72) Inventors: Akehiko Uchiyama, Kawasaki (JP); Kazuaki Umekawa, Machida (JP)

(73) Assignee: CANON KABUSHIKI KAISHA, Tokyo (JP)

(*) Notice: Subject to any disclaimer, the term of this patent is extended or adjusted under 35 U.S.C. 154(b) by 30 days.

(21) Appl. No.: 16/269,657

(22) Filed: Feb. 7, 2019

(65) Prior Publication Data
US 2019/0247003 A1    Aug. 15, 2019

(30) Foreign Application Priority Data
Feb. 15, 2018   (JP) .................................. 2018-025354

(51) Int. Cl.
*A61B 6/00*    (2006.01)
*H04N 5/32*    (2006.01)

(52) U.S. Cl.
CPC ............... *A61B 6/563* (2013.01); *A61B 6/40* (2013.01); *A61B 6/4208* (2013.01); *H04N 5/32* (2013.01)

(58) Field of Classification Search
None
See application file for complete search history.

(56) References Cited

U.S. PATENT DOCUMENTS

| 7,894,575 | B2 | 2/2011 | Tsubota et al. |
| 8,952,332 | B2 | 2/2015 | Uchiyama |
| 9,551,794 | B2 | 1/2017 | Uchiyama |
| 10,052,071 | B2 | 8/2018 | Ishioka et al. |
| 2016/0038114 | A1* | 2/2016 | Tajima ................. A61B 6/4283 378/62 |
| 2017/0272670 | A1 | 9/2017 | Tezuka et al. |
| 2018/0263572 | A1 | 9/2018 | Ishioka et al. |

FOREIGN PATENT DOCUMENTS

JP    2010-081960    4/2010

* cited by examiner

*Primary Examiner* — Hoon K Song
(74) *Attorney, Agent, or Firm* — Venable LLP

(57) ABSTRACT

A radiation imaging apparatus acquires image data by detecting radiation emitted by a radiation generation apparatus, manages a time in the radiation imaging apparatus, generates a synchronization control message to be transmitted to synchronize a time managed by an irradiation control apparatus configured to control radiation irradiation by the radiation generation apparatus with the managed time, and transmits the image data and the synchronization control message, wherein the synchronization control message is transmitted with priority over the image data.

12 Claims, 10 Drawing Sheets

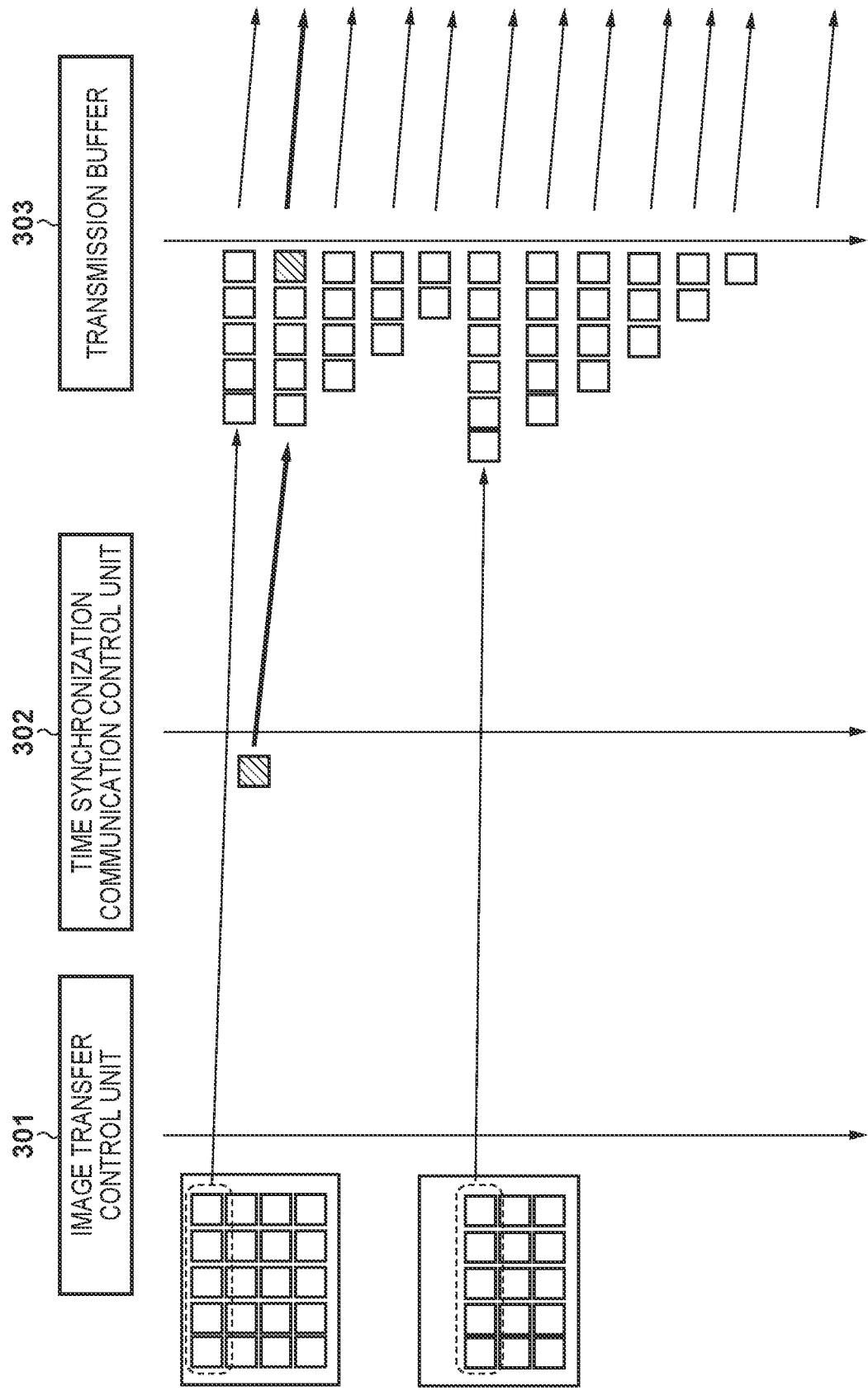

| ROW NUMBER | TRANSMISSION DATA | NEXT ROW NUMBER |
|---|---|---|
| 0 | (EMPTY) | — |
| 1 | IMAGE DATA 0 | 2 |
| 2 | IMAGE DATA 1 | 3 |
| 3 | IMAGE DATA 2 | 4 |
| 4 | IMAGE DATA 3 | End |
| 5 | (EMPTY) | — |
| 6 | (EMPTY) | — |
| 7 | (EMPTY) | — |

STATE OF NETWORK INTERFACE: PROCESSING OVER ROW NUMBER 1 OF BUFFER

- STORE MESSAGE TO EMPTY ROW 5
- PAUSE NETWORK INTERFACE
- WRITE VALUE (3) WHICH IS IN next OF ROW 2 ON next OF ROW 5
- CHANGE/ADJUST next OF ROW 2 TO 5
- RELEASE PAUSE

| ROW NUMBER | TRANSMISSION DATA | NEXT ROW NUMBER |
|---|---|---|
| 0 | (EMPTY) | — |
| 1 | (EMPTY) | — |
| 2 | IMAGE DATA 1 | 5 |
| 3 | IMAGE DATA 2 | 4 |
| 4 | IMAGE DATA 3 | End |
| 5 | TIME COMMUNICATION MESSAGE | 3 |
| 6 | (EMPTY) | — |
| 7 | (EMPTY) | — |

STATE OF NETWORK INTERFACE: RESUME PROCESSING FROM ROW NUMBER 2 OF BUFFER

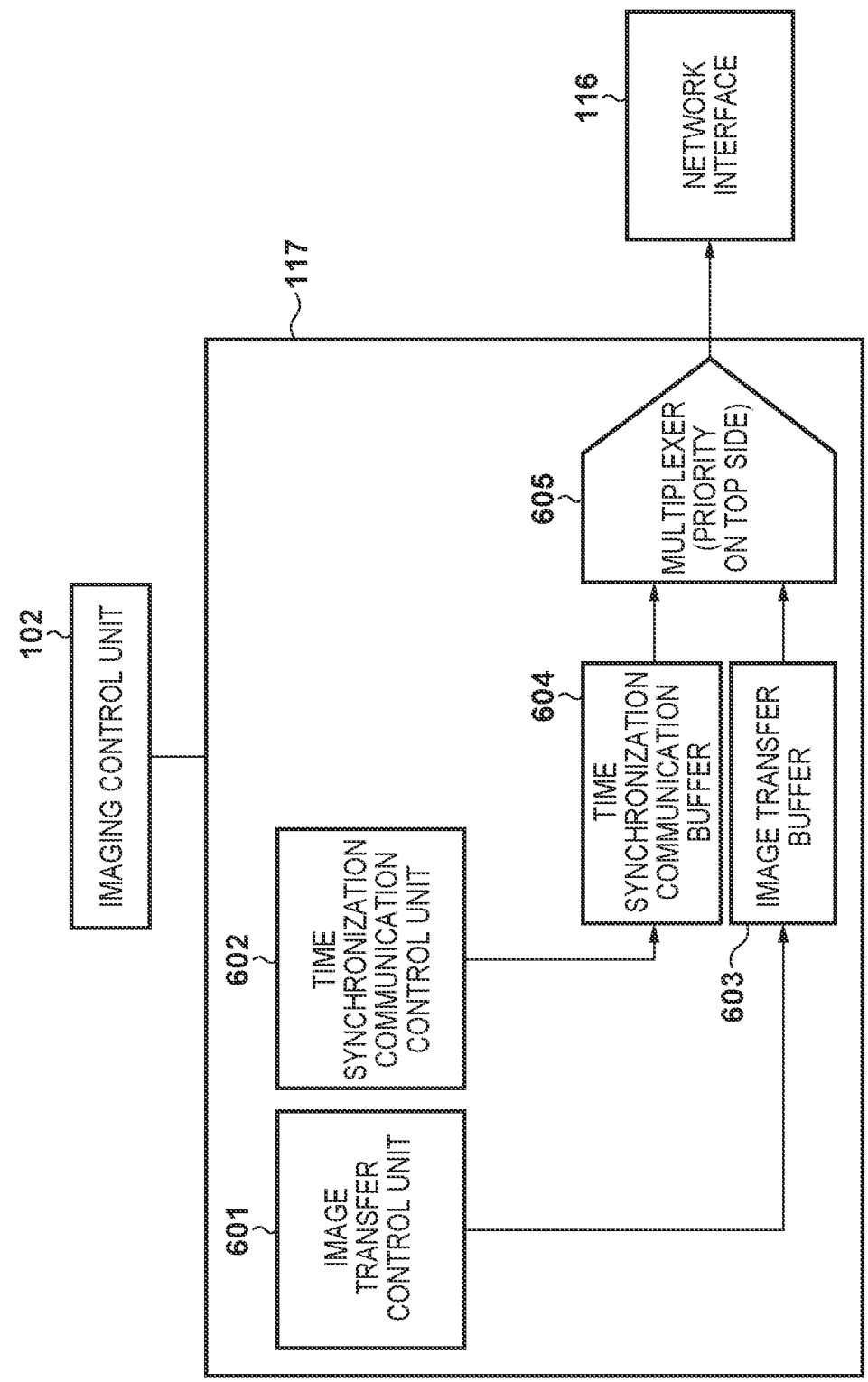

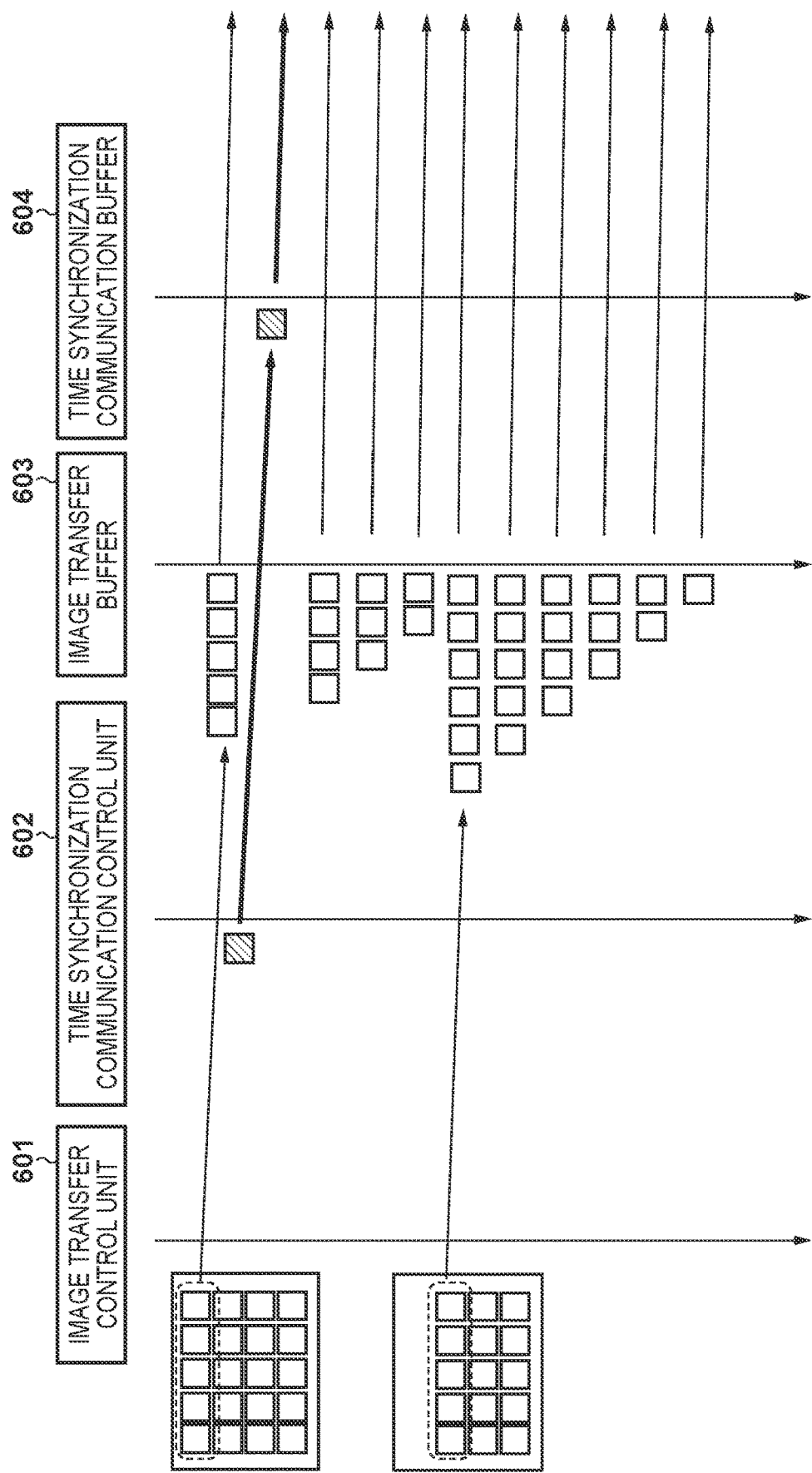

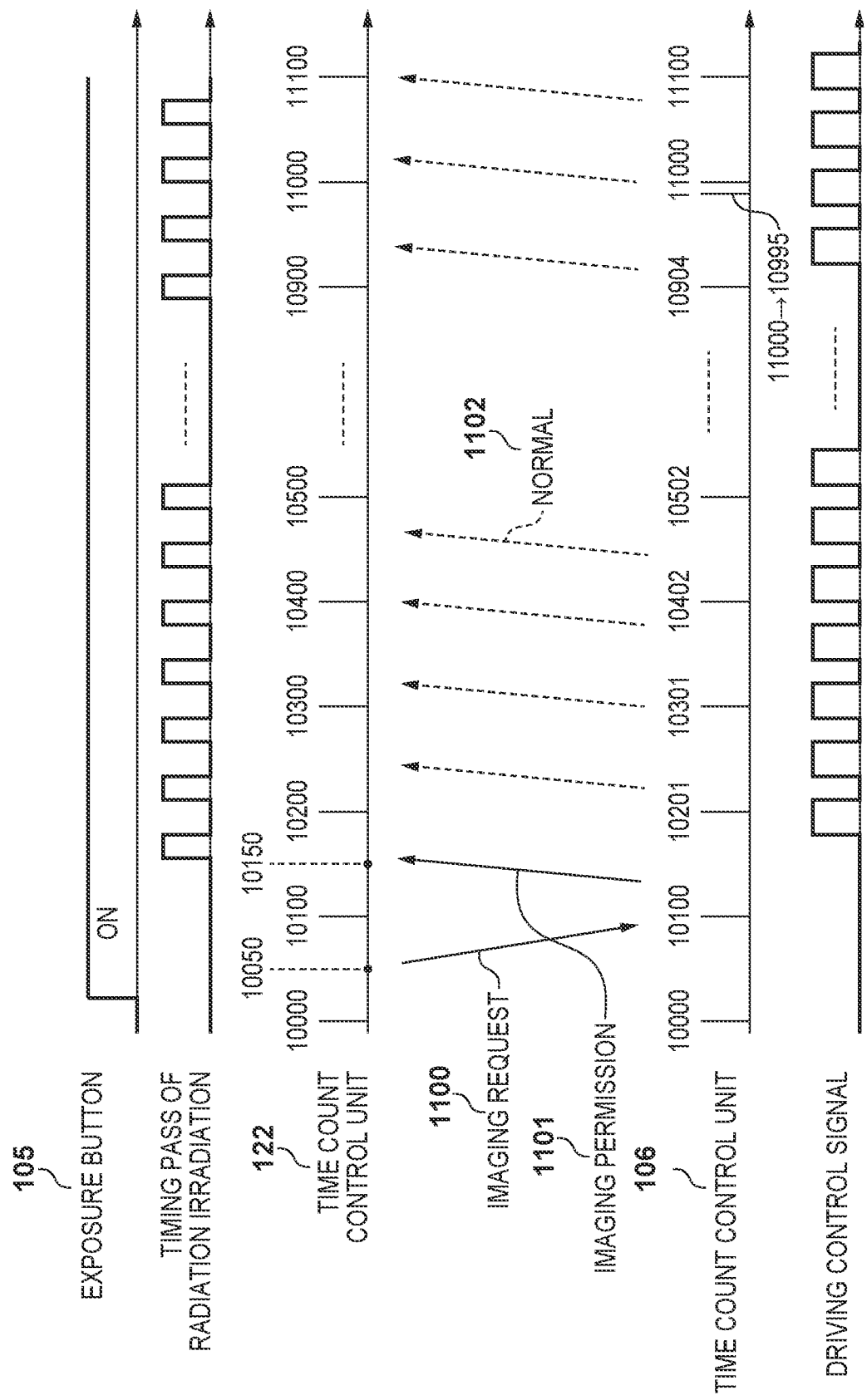

RADIATION IMAGING APPARATUS, METHOD OF CONTROLLING RADIATION IMAGING APPARATUS, RADIATION IMAGING SYSTEM, AND NON-TRANSITORY COMPUTER-READABLE STORAGE MEDIUM

BACKGROUND OF THE INVENTION

Field of the Invention

The present invention relates to a radiation imaging apparatus, a method of controlling a radiation imaging apparatus, a radiation imaging system, and a non-transitory computer-readable storage medium.

Description of the Related Art

Conventionally, a radiation imaging apparatus that detects radiation emitted by a radiation generation apparatus and transmitted through an object, generates a radiation image by digitizing the intensity distribution of the detected radiation, and obtains a clear radiation image by performing image processing for the generated radiation image has been put into practical use. Such an image processing apparatus generally uses a two-dimensional solid-state image sensor for a radiation detector (image receiver).

In general, a solid-state image sensor operates by repeating accumulation of charges corresponding to incident light, readout of the accumulated charges, and reset. In a case in which an image sensor without an electronic shutter is used, if light incidence occurs during charge readout or reset, the radiation image may be damaged. In particular, when such an image sensor is used in a radiation imaging system for medical use, the object may suffer a disadvantageous effect such as undesirable exposure. For this reason, it is preferable to synchronize the operation timing of the image sensor of the radiation detector with the radiation irradiation timing of the radiation generation apparatus.

Japanese Patent Laid-Open No. 2010-081960 describes that a radiation source control apparatus including a first time count means and a radiation imaging apparatus including a second time count means synchronized with the first time count means perform time synchronization to synchronize the end of reset with the exposure start time and the end of accumulation with the exposure end timing.

In Japanese Patent Laid-Open No. 2010-081960, the radiation source control apparatus and the radiation imaging apparatus perform communication for time synchronization and communication for image transfer using the same network during capturing of a moving image. Hence, since the timing of the communication for time synchronization and the timing of the communication for image transfer overlap, the error of time for time synchronization becomes large, and a time lag readily occurs between the radiation source control apparatus and the radiation imaging apparatus.

SUMMARY OF THE INVENTION

The present invention has been made in consideration of the above-described problem, and provides a technique of reducing a time lag between a radiation source control apparatus and a radiation imaging apparatus.

According to one aspect of the present invention, there is provided a radiation imaging apparatus which comprises: an acquisition unit configured to acquire image data by detecting radiation emitted by a radiation generation apparatus; a time count control unit configured to manage a time in the radiation imaging apparatus; a generation unit configured to generate a synchronization control message to be transmitted to synchronize a time managed by an irradiation control apparatus configured to control radiation irradiation by the radiation generation apparatus with the time managed by the time count control unit; and a transmission unit configured to transmit the image data and the synchronization control message, wherein the transmission unit transmits the synchronization control message with priority over the image data.

Further features of the present invention will become apparent from the following description of exemplary embodiments (with reference to the attached drawings).

BRIEF DESCRIPTION OF THE DRAWINGS

FIG. 4 shows an example in which a synchronization control message is output to a network interface 116 with priority over image data;

FIGS. 5A and 5B show order tables for a transmission buffer 303;

FIG. 6 shows the arrangement of a communication control unit 117 according to the second embodiment;

FIG. 7 shows an example in which communication of a synchronization control message is processed as an interrupt in transfer of image data;

FIG. 11 shows the procedure of time correction processing according to the third embodiment.

DESCRIPTION OF THE EMBODIMENTS

The embodiments of the present invention will now be described in detail with reference to the accompanying drawings. Details of structures shown in each embodiment are not limited to those shown in the specification and drawings. Note that radiation includes not only X-rays but also α-rays, β-rays, γ-rays, and various kinds of particle beams.

[Arrangement of Radiation Imaging System 100]

Figure 1:
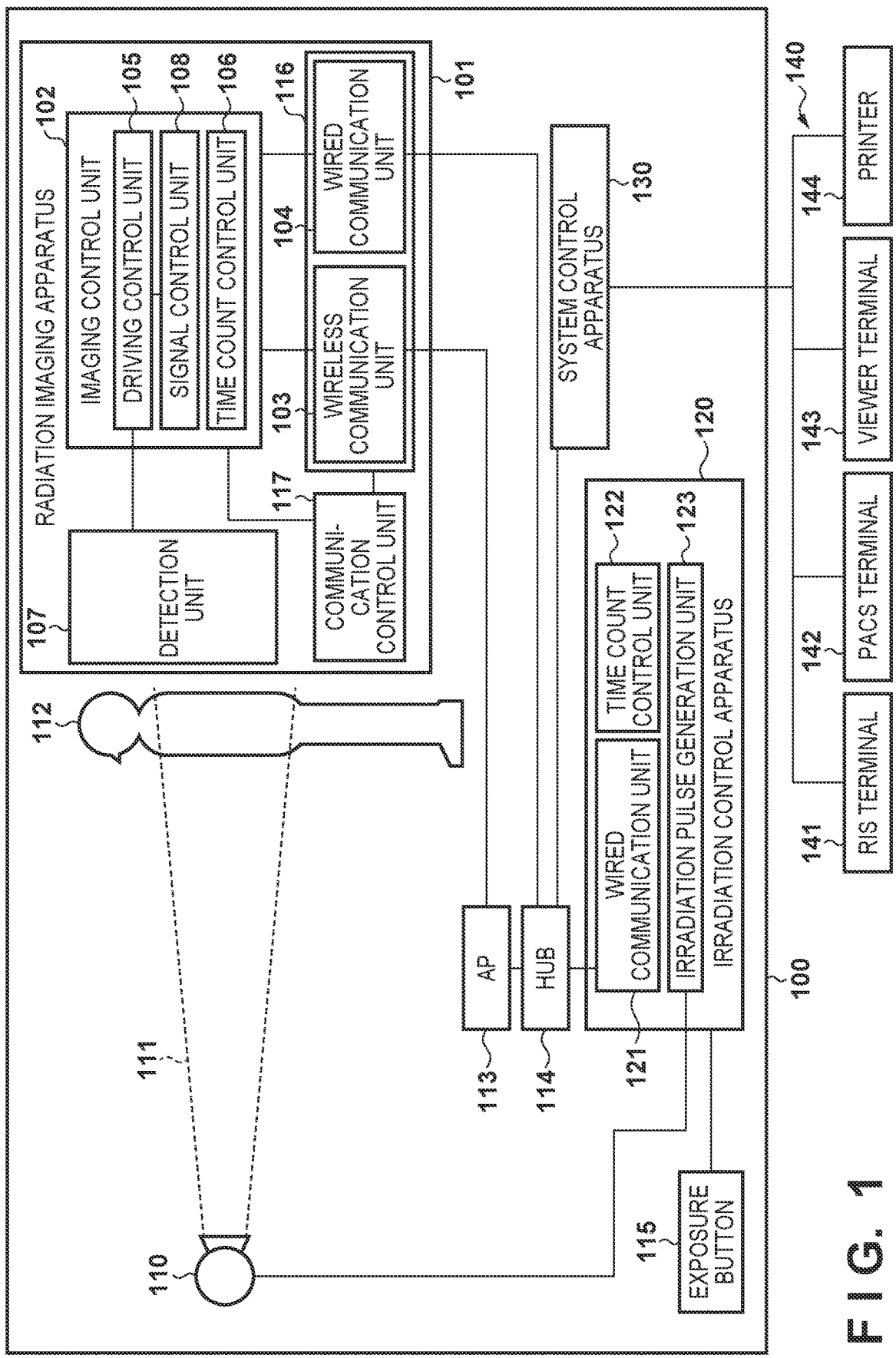
FIG. 1 shows the schematic arrangement of a radiation imaging system 100.

FIG. 1 shows the schematic arrangement of a radiation imaging system 100 according to several embodiments to be described below. The radiation imaging system 100 includes a radiation imaging apparatus 101, a radiation generation apparatus 110, an irradiation control apparatus 120, and a system control apparatus 130.

As a schematic operation, an operator inputs operation conditions of the system via an operation device (a RIS terminal 141 and the like). The pieces of information of the input operation conditions are transmitted to the radiation imaging apparatus 101 or the irradiation control apparatus 120 via the system control apparatus 130. The radiation generation apparatus 110 emits radiation in accordance with pressing of an exposure button 115 by the operator. The radiation radiated by the radiation generation apparatus 110 passes through a subject and is then detected by the radiation imaging apparatus 101. The radiation imaging apparatus 101 generates a radiation image from the detected radiation and transfers it to the system control apparatus 130. The system control apparatus 130 outputs the received radiation image to a PACS terminal 142, a viewer terminal 143, or a printer 144.

Each constituent element of the radiation imaging system 100 will be described next. The irradiation control apparatus 120 functions as a radiation source control apparatus. A wired communication unit 121 receives a signal transmitted from the system control apparatus 130, or transmits/receives a signal to/from the radiation imaging apparatus 101. A time count control unit 122 manages and controls the information (time information) of time that progresses. The time count control unit 122 can manage time to enable adjustment of (charge accumulation time–radiation irradiation time)/2/10 or less. An irradiation pulse generation unit 123 generates a timing signal (timing pulse) of radiation irradiation based on the time information managed by the time count control unit 122 and outputs the timing signal to the radiation generation apparatus 110.

The radiation generation apparatus 110 functions as a radiation source and includes a bulb and irradiation and diaphragm mechanisms. Based on the timing pulse from the irradiation control apparatus 120, the radiation generation apparatus 110 generates (emits) radiation 111 in pulses or continuously. The radiation generation apparatus 110 can also include an imaging means and a display means for displaying an imaging condition and a captured image.

The radiation imaging apparatus 101 includes a detection unit 107, an imaging control unit 102, a network interface 116, and a communication control unit 117. The detection unit 107 includes a two-dimensional solid-state image sensor and converts radiation into an electrical signal to acquire a radiation image. The imaging control unit 102 includes a driving control unit 105, a signal control unit 108, and a time count control unit 106. The driving control unit 105 performs driving control (control of charge accumulation and readout) of the detection unit 107. The signal control unit 108 performs various kinds of image processing for the radiation image acquired by the detection unit 107, thereby generating a radiation image after image processing. The time count control unit 106 manages and controls time information. The network interface 116 includes a wireless communication unit 103 and a wired communication unit 104. The radiation image generated by the signal control unit 108 is transferred to the system control apparatus 130 via the wireless communication unit 103 and/or the wired communication unit 104 and used for inspection or the like. The communication control unit 117 connects the imaging control unit 102 and the network interface 116 and controls communication for radiation image transfer and time synchronization.

The radiation imaging apparatus 101, the irradiation control apparatus 120, and the system control apparatus 130 are connected to each other via a wireless or wired communication network. The communication network includes a wireless LAN access point (AP) 113 and a HUB 114. Information is exchanged in the form of a message between the devices connected via the communication network. The communication control unit 117 determines the connection state of the wired communication unit 104 or the wireless communication unit 103. For example, in a wired connection state, communication can automatically switch to wired communication. Note that although a system including both a wireless method and a wired method has been described, a system can also be formed using one of communication methods.

On the other hand, the radiation generation apparatus 110 and the irradiation control apparatus 120 are electrically connected directly without intervention of a communication network. For this reason, information is directly transmitted as an electrical signal without being converted into the form of a message. In addition, an electrical signal is directly transmitted between the irradiation control apparatus 120 and the exposure button 115 as well.

The radiation imaging system 100 is connected to the RIS terminal 141, the PACS terminal 142, the viewer terminal 143, and the printer 144 via a communication means 140 such as a network. Note that RIS represents Radiology Information System, and PACS represents Picture Archiving and Communication System.

The RIS terminal 141 is an operation terminal connected to the radiation imaging system 100 and forms an information system in a department of radiography. This information system is an information management system that comprehensively manages, for example, radiation images or information (additional information) added to an inspection order (inspection instruction) input by the operator. The additional information includes inspection information including an inspection ID or a receipt number. The inspection information includes imaging protocol information. The imaging protocol includes parameter information or imaging execution information used at the time of imaging, image processing, or the like, and imaging environment information such as a sensor type or an imaging posture. The radiation imaging system 100 copes with at least one of a still image and a moving image of a radiation image. In particular, for example, parameters such as a frame rate and the length of a radiation pulse per frame are set for the imaging protocol for capturing of a moving image. In addition, the inspection information includes information for specifying an inspection order such as an inspection ID or a receipt number and information for specifying a radiation image according to the inspection order.

The operator can input the inspection order via the RIS terminal 141, and the radiation imaging system 100 can perform imaging in accordance with the input inspection order. The input inspection order can be stored and managed by the RIS terminal 141, but may be stored and managed by a server (not shown) connected to the MS terminal 141 and the radiation imaging system 100. Note that the input inspection order may be stored and managed by the system control apparatus 130 or the like in the radiation imaging system 100.

The PACS terminal 142 saves and manages a radiation image generated by the radiation imaging apparatus 101. That is, the PACS terminal 142 functions as a part of an image management system configured to manage captured images. The viewer terminal 143 can display and output a radiation image saved in the PACS terminal 142. The printer 144 can output a radiation image saved in the PACS terminal 142 to a medium such as a film.

The operator of the radiation imaging system 100 presses the exposure button 115 at a timing to execute imaging. The occurrence of pressing of the exposure button 115 is transmitted to the irradiation control apparatus 120 as an electrical signal. The irradiation control apparatus 120 generates a message representing the start of imaging in accordance with the electrical signal transmitted from the exposure button 115, and transmits the message to the radiation imaging apparatus 101 via the communication network. The message includes the information of time of the imaging start (irradiation start).

When an imaging permission message to the imaging start message is transmitted from the radiation imaging apparatus 101 to the irradiation control apparatus 120, the time of the imaging start is shared by the radiation imaging apparatus 101 and the irradiation control apparatus 120. After that, the irradiation pulse generation unit 123 in the irradiation control apparatus 120 generates a timing pulse of radiation irradiation. The irradiation pulse generation unit 123 generates the timing pulse based on time information managed by the time count control unit 122. The timing pulse is transmitted to the radiation generation apparatus 110, and the radiation generation apparatus 110 emits the radiation 111 in accordance with the timing pulse.

On the other hand, after the radiation imaging apparatus 101 receives the message representing the imaging start, the driving control unit 105 in the imaging control unit 102 generates a driving control signal representing a driving (charge readout) timing to the detection unit 107. The driving control signal is transmitted to the detection unit 107 and the detection unit 107 operates in accordance with the driving control signal. The time count control unit 106 in the radiation imaging apparatus 101 manages time information. The driving control unit 105 generates the driving control signal based on the time information in the time count control unit 106.

When the operator of the radiation imaging system 100 stops pressing the exposure button 115 to end the imaging, the irradiation control apparatus 120 stops generation of the timing pulse and generates a message representing the stop of imaging. The message is exchanged with the radiation imaging apparatus 101.

In the above-described operation, acquisition of the radiation image is preferably executed by selecting a time that does not overlap the timing pulse of radiation irradiation. That is, acquisition of the radiation image is preferably performed in a time zone different from the time zone of radiation irradiation. To implement such an exclusive time relationship, times managed by the time count control unit 122 in the irradiation control apparatus 120 and the time count control unit 106 in the radiation imaging apparatus 101 need to be correctly synchronized. However, because of, for example, the characteristics of a quartz oscillator, the time count control unit 122 and the time count control unit 106 deviate from the standard time in accordance with the elapsed time or temperature.

Figure 2:
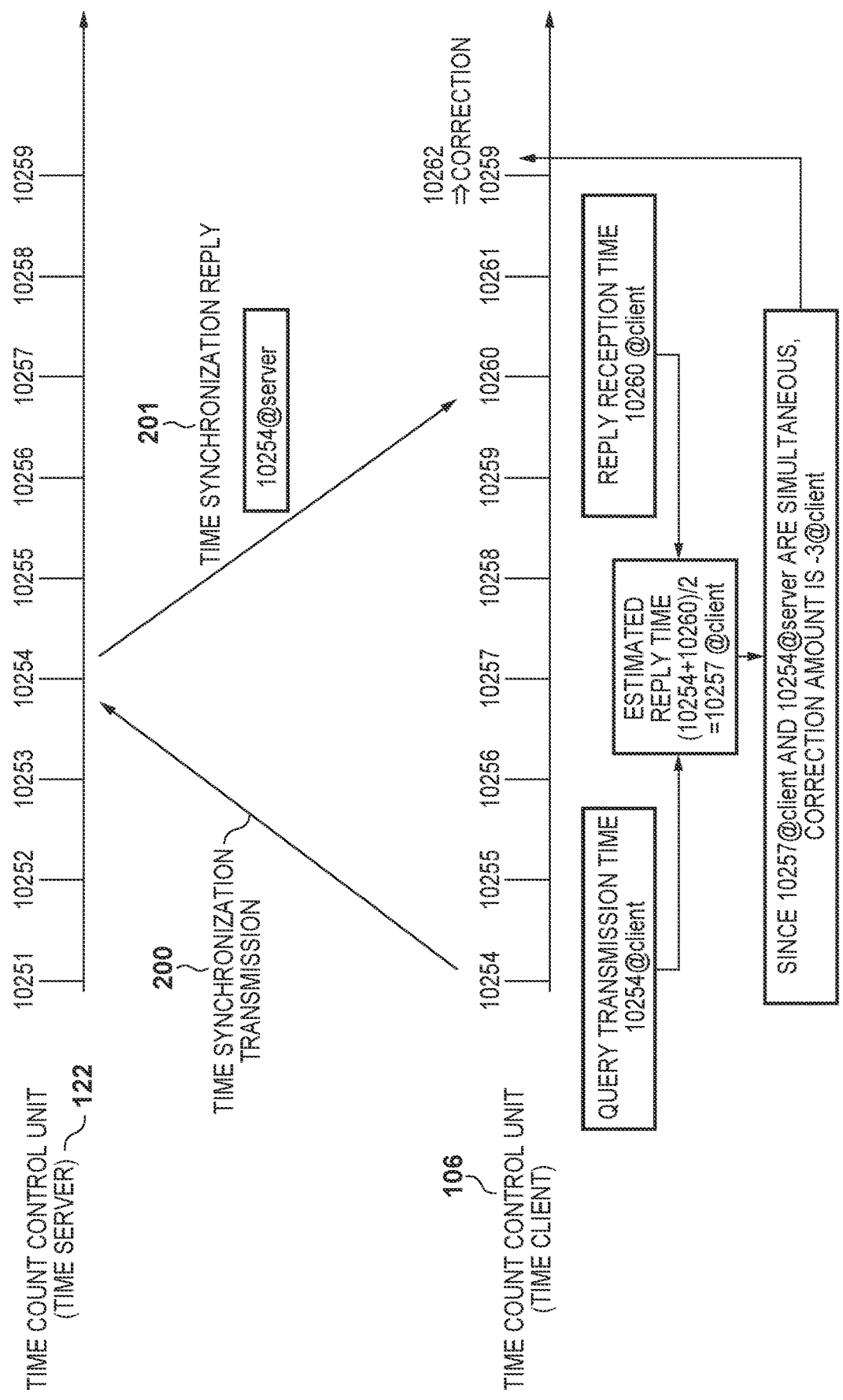
FIG. 2 is a view showing a procedure of synchronizing times.

FIG. 2 shows a procedure of establishing synchronization of times managed by the time count control unit 106 in the radiation imaging apparatus 101 and the time count control unit 122 in the irradiation control apparatus 120 by communication on the network. For the description, assume that the time count control unit 122 operates as a time server that becomes the reference of time synchronization, and the time count control unit 106 operates as a time client that operates following the time server. Additionally, in FIG. 2, the abscissa represents a time base, and a number on the time base represents a time value.

First, the time count control unit 106 in the radiation imaging apparatus 101 transmits a message (query message) for inquiring the time of the server to the irradiation control apparatus 120 via the wired communication unit 104 or the wireless communication unit 103. At this time, the time count control unit 106 acquires the time of query message transmission. In the example shown in FIG. 2, the time count control unit 106 acquires a time value "10254". Upon receiving the query message via the wired communication unit 121, the time count control unit 122 in the irradiation control apparatus 120 immediately returns a message (reply message). At this time, the time count control unit 122 acquires the time of reply message transmission and includes it into the reply message. In the example shown in FIG. 2, the time count control unit 122 includes the time value "10254" into the reply message.

Upon receiving the reply message from the irradiation control apparatus 120, the time count control unit 106 in the radiation imaging apparatus 101 acquires the time of reply message reception. In the example shown in FIG. 2, the time count control unit 106 acquires a time value "10260". If the propagation time of the query message and the propagation time of the reply message are assumed to equal, the time of return of the reply message by the irradiation control apparatus 120 can be estimated as the intermediate value between the time value "10254" of transmission and the time value "10260" of reception, that is, (10254+10260)/2=10257 in the time managed by the time count control unit 106.

By the way, since the time value included in the reply message is 10254, the difference from the time (estimated) of return of the reply message by the irradiation control apparatus 120 is calculated as 10257−10254=3. That is, the time of the radiation imaging apparatus 101 leads by 3 in the time value. In this way, the difference between the times managed by the time count control unit 106 and the time count control unit 122 is calculated as a correction value, and the time managed by the time count control unit 106 is corrected by the correction value, thereby synchronizing the times managed by the time count control unit 106 and the time count control unit 122.

Note that in the example shown in FIG. 2, the correction value for time synchronization is calculated based on only one query. Since the propagation time can fluctuate in fact, the correction value based on only one query may deviate from the true amount. For this reason, the correction value may be calculated statistically by executing a plurality of queries. For example, a predetermined number of time differences or correction values are collected in ascending order of round trip time (the time from query transmission to reply reception) from a plurality of queries, and an average is calculated.

In the example shown in FIG. 2, the propagation time of the query message and the propagation time of the reply message are assumed to equal. However, since the radiation image obtained by imaging and the message used to synchronize the times are output from the wired communication unit 104 or the wireless communication unit 103 of the radiation imaging apparatus 101 in a mixed manner particularly during capturing of a moving image, the message used to synchronize the times may delay. When the delay occurs, a correct time difference cannot be calculated, and the times managed by the time count control unit 122 and the time count control unit 106 are not synchronized. As a result, the time balance between driving control of the radiation imaging apparatus 101 and radiation irradiation by the radiation generation apparatus 110 may be lost.

An arrangement capable of synchronizing times managed by the time count control unit 122 and the time count control unit 106 even during capturing of a moving image will be described in the following embodiments.

First Embodiment

As described above, in this system, various kinds of information are transmitted via a network via an AP 113 or a HUB 114. A radiation image obtained by imaging, messages exchanged to control the start and end of imaging, and a query message and a reply message used to synchronize times have already been described above. In addition, a command for transmitting preset information, a message for reporting abnormality or normality of each apparatus, and the like can also exist. In a radiation imaging apparatus 101, these pieces of information can be transmitted/received from/to a wired communication unit 104 or a wireless communication unit 103.

These pieces of information transmitted via the network pass through the same medium or means but have characteristics different from each other. For example, a radiation image is formed by an enormous amount of data and can be divided into a number of packets and transmitted. In addition, a gap period is provided between transfer of one radiation image and transfer of the next radiation image. Unless the gap period is expired, no problem is posed even if transfer processing of the radiation image delays. On the other hand, the message used to synchronize the times is formed by a few packets. Since a delay of packets directly appears as the error of the estimated time difference between the time count control units, the packets are preferably transmitted without a delay as much as possible.

As the first embodiment, the radiation imaging apparatus 101 that gives higher priority to communication for time synchronization than transfer (transmission) of a radiation image will be described with reference to FIGS. 3, 4, 5A, and 5B. Note that as for the radiation imaging apparatus 101 according to this embodiment, transmission processing of a radiation image will be described.

Figure 3:
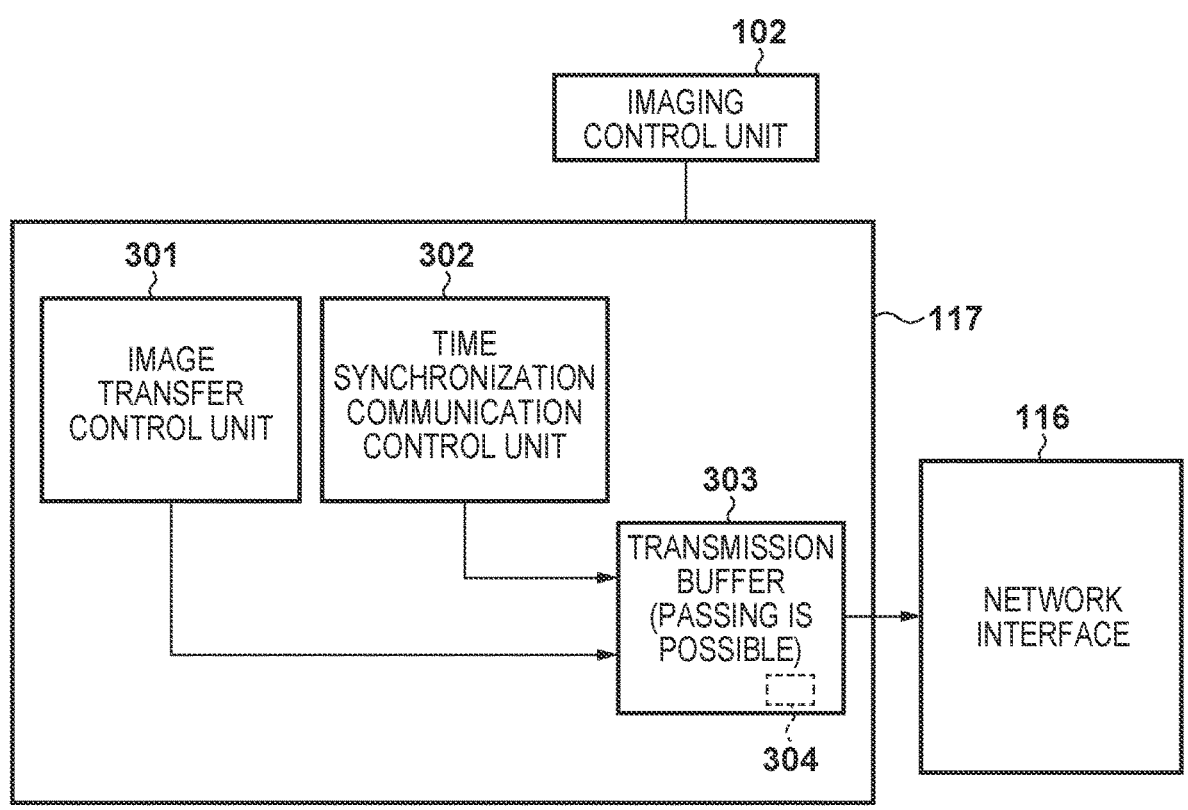
FIG. 3 shows the arrangement of a communication control unit 117 according to the first embodiment.

FIG. 3 shows the arrangement of a communication control unit 117 in the radiation imaging apparatus 101 according to this embodiment. The communication control unit 117 according to this embodiment includes an image transfer control unit 301, a time synchronization communication control unit 302, and a transmission buffer 303. In addition, the communication control unit 117 may include a table management unit 304 indicated by a dotted line to perform order control to be described later with reference to FIGS. 5A and 5B.

The image transfer control unit 301 operates in cooperation with a signal control unit 108, and the time synchronization communication control unit 302 operates in cooperation with a time count control unit 106. The image transfer control unit 301 and the time synchronization communication control unit 302 store image data (radiation image) and a synchronization control message (a query message used to synchronize times) in the transmission buffer 303 in accordance with communication procedures. The image data and the synchronization control message stored in the transmission buffer 303 are sequentially extracted and supplied to a network interface 116. At this time, the transmission buffer 303 operates to preferentially output the synchronization control message over the image data independently of the order of storage in the transmission buffer 303.

An example of adjustment of the transmission order according to this embodiment will be described next with reference to FIG. 4. FIG. 4 shows an example in which the synchronization control message stored in the transmission buffer 303 after the image data is output to the network interface 116 with priority over the image data. As shown in FIG. 4, even when the packets constructing image data are sequentially being transferred, if the synchronization control message is stored in the transmission buffer 303, the synchronization control message is output to the network interface 116 without a delay. Since the synchronization control message preferentially interrupts into the packets of the image data, the progress of transfer of the image data delays.

Another example of adjustment of the transmission order will be described next with reference to FIGS. 5A and 5B. FIGS. 5A and 5B show order tables 501 and 502 for the transmission buffer 303, which are referred to by the network interface 116. These tables are generated and managed by the table management unit 304 in the transmission buffer 303.

The order table 501 (and also the order table 502) has a form divided into a plurality of rows and columns. In each row of the order table 501, at least a column (to be referred to as a data column hereinafter) that stores image data/synchronization control message to be transmitted and a column (to be referred to as a next column hereinafter) that designates a row number to be processed next after the processing of the contents of the row exist. The order table 501 shown in FIG. 5A shows a table of the transmission buffer formed by, for example, eight rows. Previously stored image data are stored in rows of row numbers 1 to 4. As for the next columns of these rows, the row numbers are written at the time of image data storage like next=2 for row 1, next=3 for row 2, . . . such that the image data are sequentially continuously processed. In the next column of the already stored last image data (image data 3 shown in FIG. 5A), an END mark is written to show the absence of subsequent data. In the remaining rows, all columns are blank because data is never written, or data is erased after the transmission processing of written data.

The network interface 116 sequentially performs transmission while referring to the order table 501. After the data column of a given row is referred to, and image data corresponding to the row is transmitted, the number of the row to be processed next is obtained by referring to the next column of the row. When the reference to the next column ends, the row becomes unnecessary, and the columns are returned to blank. After that, the network interface 116 starts referring to the next row. The procedure is repeated in a similar manner, and upon detecting an END mark in the next column, the network interface 116 is set in pause state.

The procedure of rewriting the order table by storing image data in the transmission buffer 303 during the reference and transmitting operation of the network interface 116 is as follows. That is, referring to FIG. 5A, the table management unit 304 first searches for a blank row in the order table 501 and stores additional transmission data, for example, the continuation of the image data in the data column of the row. In addition, the table management unit 304 writes the END mark in the next column of the row. Next, the table management unit 304 removes the END mark in the row having the END mark so far and, instead, writes the row number of the row in which the additional write has been executed. With this procedure, the image data additionally registered in the order table is transmitted next to the transmission of already registered image data.

However, when storing the synchronization control message in the transmission buffer 303, the procedure is partially different from the above-described procedure. This procedure will be described while comparing FIGS. 5A and 5B. The procedure of searching for a blank row in the order table and storing the synchronization control message in the data column by the table management unit 304 is the same as the above-described procedure. However, adjustment of the next column is different from the above-described procedure.

First, the communication control unit 117 obtains the row number of the row for which the network interface 116 is executing processing. The communication control unit 117 causes the network interface 116 to pause so the processing does not simultaneously overtake the row. In the example shown in FIG. 5A, since the network interface 116 that is processing row number 1 pauses, image data corresponding to row number 2 to be processed next is not read from the network interface 116 yet. Hence, if the table is changed now, the processing can correctly be performed. Hence, the table management unit 304 changes the next column of row number 2 and writes, as a row number to be processed next, 5 that is a newly added row number. On the other hand, for the next column of row number 5, the table management unit 304 writes the value originally written in the next column of row number 2, that is, row number 3 in this example so as to resume the processing of the row in which image data is already stored. Finally, the communication control unit 117 resumes the network interface 116 that has paused, and the procedure ends. As a result of adjustment done by this procedure, the order table 502 shown in FIG. 5B is obtained, and the synchronization control message is processed as an interrupt between image data 1 and image data 2. As described above, the synchronization control message addition procedure (the change from FIG. 5A to FIG. 5B) is different from the image data addition procedure in that the adjustment of the next column is performed such that data is added to a row after the END mark or a row near the row currently under processing.

Note that in the above description, an example in which the transmission order of the synchronization control message is adjusted such that it is transmitted next to image data 1 (next to row number 2). This is because the network interface 116 is assumed to pause on a row basis for the descriptive convenience. If the pause of the network interface 116 can be designated by more detailed conditions, and the network interface 116 can pause immediately before the read of the next column of row number 1, adjustment can also be performed such that the synchronization control message is transmitted next to image data 0 (next to row number 1). In this case, the transmission delay of the synchronization control message can be made shorter.

In addition, the term "pause" does not mean requesting complete stop of the network interface 116, and reference to the next row (or reference to the next column of the current row) need only be impeded. Hence, even after reception of a pause instruction, the network interface 116 can continuously execute transmission of the data of the current row in progress. If the procedure of write (registration) in the order table is completed in a short time, the stop of the network interface 116 is substantially not performed, and the utilization rate of the network interface does not lower.

The method of adjusting the transmission order in the table format has been described above with reference to FIGS. 5A and 5B. In this method, some procedures such as exclusive processing concerning the reference to the table and rewrite of each column of the table are executed. For this reason, this method is suitable to hold an order table as a data structure on a storage device and execute maintenance of the table by software processing from a microprocessor or the like. However, the processing may be executed by hardware such as a logic circuit, as a matter of course.

Additionally, in the description of FIGS. 5A and 5B, actual transmission data is stored in a transmission data column of the order table. However, an actual table need not have such a structure. The entity of transmission data may be stored in another place on the storage device, and only position information may be described in the order table.

As described above, in this embodiment, even if the occurrence of communication of the synchronization control message overlaps the transfer period of a radiation image, the transmission delay of the synchronization control message is suppressed. For this reason, the time error between the time count control units of the radiation imaging apparatus 101 and an irradiation control apparatus 120 can be decreased. It is therefore possible to accurately and easily synchronize a radiation generation apparatus 110 and the radiation imaging apparatus 101.

Second Embodiment

As the second embodiment, a form different from the first embodiment, in which higher priority is given to communication for time synchronization than transfer (transmission) of a radiation image, will be described. Note that in this embodiment, a description of portions common to the first embodiment will be omitted. A point different from the first embodiment is the arrangement of a communication control unit 117.

FIG. 6 shows the arrangement of the communication control unit 117 in a radiation imaging apparatus 101 according to this embodiment. The communication control unit 117 according to this embodiment includes an image transfer control unit 601, a time synchronization communication control unit 602, an image transfer buffer 603, a time synchronization communication buffer 604, and a multiplexer 605 that operates as a selection mechanism.

The image transfer control unit 601 and the time synchronization communication control unit 602 function like the image transfer control unit 301 and the time synchronization communication control unit 302 shown in FIG. 3 described in the first embodiment, respectively. The image transfer buffer 603 operates in correspondence with the image transfer control unit 601, and the time synchronization communication buffer 604 operates in correspondence with the time synchronization communication control unit 602. Additionally, in the image transfer buffer 603 and the time synchronization communication buffer 604, stored data (image data and a synchronization control message) are extracted in the order the data are stored.

The multiplexer 605 extracts the data from the image transfer buffer 603 and the time synchronization communication buffer 604 and supplies the data to a network interface 116. At this time, the multiplexer 605 extracts data from only one of the image transfer buffer 603 and the time synchronization communication buffer 604 at once. Extraction processing is executed on a communication packet basis. During the extraction processing, the multiplexer 605 does not extract data from the other buffer. In addition, the extraction is preferentially performed from the time synchronization communication buffer 604. When the time synchronization communication buffer 604 becomes empty, data extraction from the image transfer buffer 603 is performed.

Because of the unbalanced priority, even in a state in which a number of packet data are stored in the image transfer buffer 603, the multiplexer 605 stops extraction from the image transfer buffer 603 when data is stored in the time synchronization communication buffer 604. The multiplexer 605 operates so as to transmit the data in the time synchronization communication buffer 604 first.

An example of a transmission order according to this embodiment will be described next with reference to FIG. 7. FIG. 7 shows an example in which communication of a synchronization control message is processed as an interrupt in transfer of image data. Assume that the image transfer control unit 601 stores image data, and the time synchronization communication control unit 602 stores a synchronization control message. When the time synchronization communication buffer 604 is empty, the multiplexer 605 sequentially extracts data from the image transfer buffer 603, supplies the data to the network interface 116, and causes the network interface 116 to transmit it. However, when the synchronization control message is stored in the time synchronization communication buffer 604, the multiplexer 605 extracts the synchronization control message in the time synchronization communication buffer 604 first even if image data still exists in the image transfer buffer 603, supplies the synchronization control message to the network interface 116, and causes the network interface 116 to transmit it. When the time synchronization communication buffer 604 becomes empty, the progress of transfer of image data is resumed.

Figure 8:
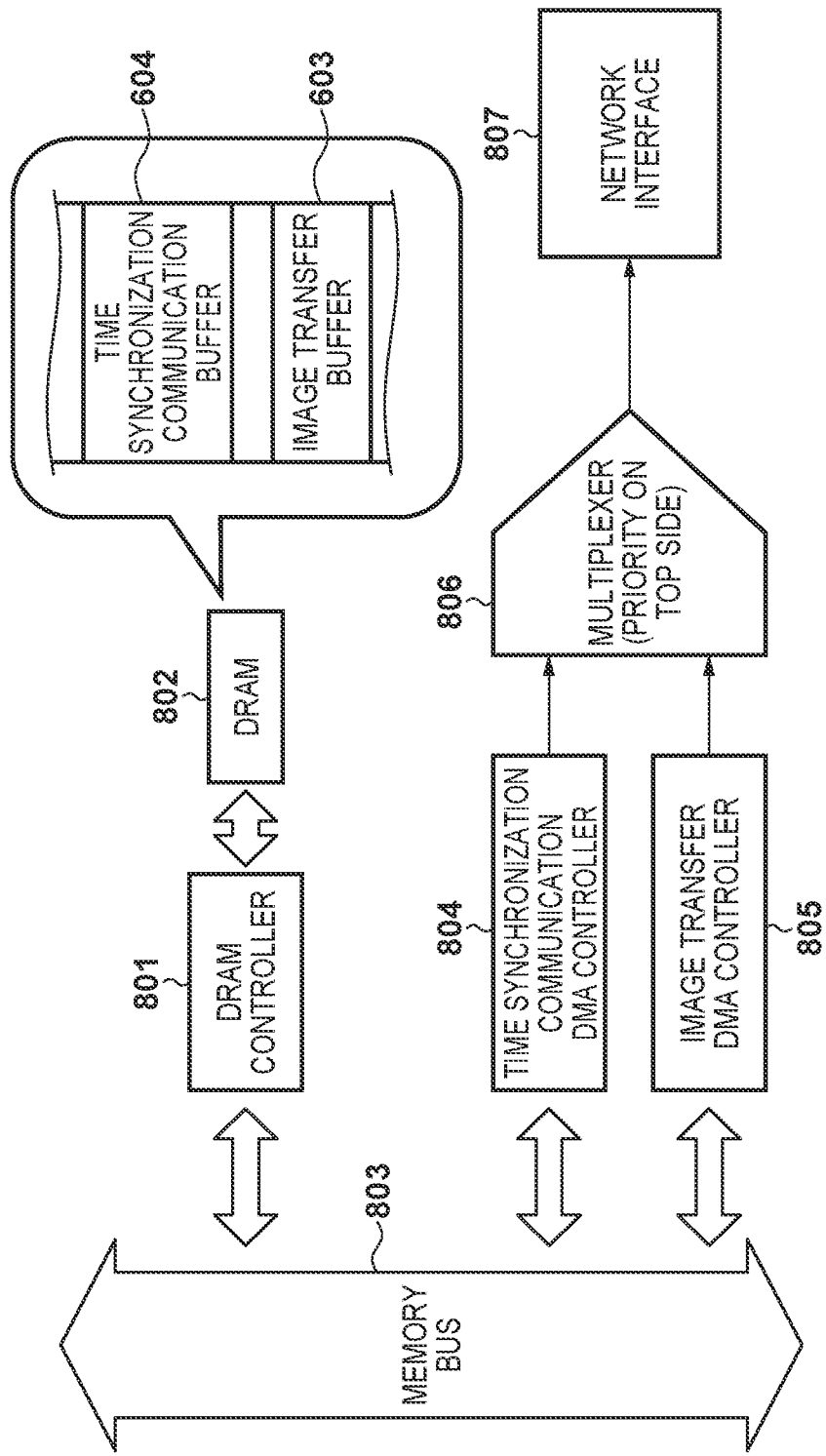
FIG. 8 shows an example of implementation of an image transfer buffer 603, a time synchronization communication buffer 604, and a multiplexer 605.

FIG. 8 shows an example of implementation of the image transfer buffer 603, the time synchronization communication buffer 604, and the multiplexer 605, which operate as shown in FIG. 7. In the arrangement shown in FIG. 8, a DRAM controller 801, DMA controllers 804 and 805, a memory bus 803, a multiplexer 806, and a network interface 807 are integrated on, for example, ASIC or FPGA. A DRAM 802 read/write-accessed by the DRAM controller 801 operates as a large storage capacity. The DMA controllers 804 and 805 are provided individually for time synchronization communication and image transfer and connected to the DRAM controller 801 via the memory bus 803. Each of the DMA controllers 804 and 805 for time synchronization communication and image transfer read-accesses the DRAM 802 via the DRAM controller 801, converts the readout data into stream data in time order, and supplies it to the multiplexer 806 via a stream bus. The multiplexer 806 appropriately selects one of the stream signals received from the DMA controllers 804 and 805, and delivers it to the network interface 807 via the stream bus. The image transfer control unit 601 shown in FIG. 6 can access the DRAM 802 and the image transfer DMA controller 805, and the time synchronization communication control unit 602 can access the DRAM 802 and the time synchronization communication DMA controller 804.

Here, the stream bus bundles a data signal to be delivered in one direction and a hand shake signal used to adjust the speed of data delivery on both the supply side and the reception side. When the data reception side stops data reception, the data delivering side pauses processing while keeping declaring that there is an intention to deliver data. When one stream is being selected and received, the multiplexer 806 stops receiving the other stream. Hence, the DMA controller in the stop state cannot deliver data to the multiplexer and therefore pauses and also stops readout from the DRAM 802.

A state in which communication for time synchronization is processed as an interrupt in transfer of image data in the arrangement shown in FIG. 8 will be described below. First, the image transfer control unit 601 stores a number of image packet data in a specific area on the DRAM 802. The area on the DRAM 802 serves as the image transfer buffer 603. Next, the image transfer control unit 601 gives a trigger to the image transfer DMA controller 805. The image transfer DMA controller 805 starts readout from the DRAM 802, declares an intention to supply data to the stream bus, and requests the multiplexer 806 to receive. At this point of time, since only the image transfer DMA controller 805 notifies the multiplexer 806 of the data supply intention, the multiplexer 806 receives the signal from the stream bus of the image transfer DMA controller 805 and relays and delivers it to the network interface 807.

During this time, the time synchronization communication control unit 602 stores the synchronization control message in a specific area on the DRAM 802. The area on the DRAM 802 serves as the time synchronization communication buffer 604. Next, the time synchronization communication control unit 602 gives a trigger to the time synchronization communication DMA controller 804. The time synchronization communication DMA controller 804 starts readout from the DRAM 802, declares an intention to supply data to the stream bus, and requests the multiplexer 806 to receive. Note that since the memory bus 803 and the DRAM controller 801 appropriately time-divisionally perform processing even if a plurality of readout requests exist at the same time, the readout requests from the DMA controllers 804 and 805 can progress almost simultaneously.

At this point of time, the multiplexer 806 is requested by both the image transfer DMA controller 805 and the time synchronization communication DMA controller 804 to receive data via the stream bus. At this time, the multiplexer 806 stops signal reception from the stream bus at a break between the stream signals of image transfer and, more specifically, on a packet basis. Instead, the multiplexer 806 receives a signal from the stream bus for time synchronization and relays and delivers it to the network interface 807. Accordingly, the synchronization control message is transmitted as an interrupt in transfer of image data. Because of the influence of the stop of reception of the image transfer stream, the image transfer DMA controller 805 cannot deliver the data read out from the DRAM 802 to the downstream side and therefore pauses readout from the DRAM 802 as well.

Since the amount of communication contents of time synchronization communication is small, the time synchronization communication DMA controller 804 quickly completes the processing and stops signal output to the stream bus. Accordingly, the multiplexer 806 resumes reception of the image transfer stream. When the stream is resumed, the image transfer DMA controller 805 resumes readout of subsequent data from the DRAM 802 and resumes image data transfer.

An example in which the transmission order is adjusted by the multiplexer with priority has been described above with reference to FIG. 8. However, the arrangement is not limited to this. For example, although the time synchronization communication buffer 604 is formed as an area on the DRAM 802, an on-chip memory on ASIC may be used as the buffer because the amount of the contents of time synchronization communication is small. Additionally, instead of using a DMA controller to generate the stream signal of time synchronization communication, a logic circuit configured to generate packet data of time synchronization communication only by a given trigger may be provided to generate the stream signal directly without intervention of a memory. Furthermore, although most elements are formed by logic circuits in FIG. 8, the implementation is not limited to this. The transmission buffer and the multiplexer may be implemented by a storage capacity and software processing.

As described above, in this embodiment, even if the occurrence of time synchronization communication overlaps the transfer period of an image, the transmission delay of the time synchronization communication is minimized. For this reason, the synchronization error between the clocks of the radiation imaging apparatus 101 and the irradiation control apparatus 120 can be decreased. It is therefore possible to accurately and easily synchronize a radiation generation apparatus 110 and the radiation imaging apparatus 101.

Third Embodiment

In the first and second embodiments, a procedure of giving priority to communication for time synchronization over transfer of image data has been described. In this embodiment, a system that calculates and stores in advance a correction value used to synchronize times managed by a time count control unit 106 in a radiation imaging apparatus 101 and a time count control unit 122 in an irradiation control apparatus 120 and performs communication using the stored correction value during capturing of a moving image will be described.

Figure 9:
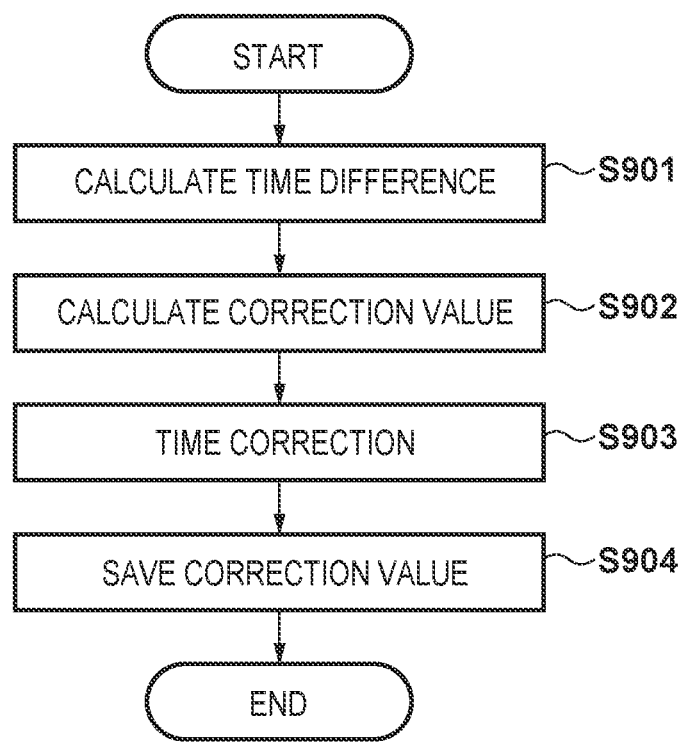
FIG. 9 shows a flowchart of time synchronization by a time count control unit 106 except during imaging according to the third embodiment.

FIG. 9 shows a flowchart of time synchronization by the time count control unit 106 except during imaging according to this embodiment. This procedure is executed at a predetermined time interval (for example, once a sec, and to be referred to as a synchronization procedure execution interval hereinafter). In step S901, the time count control unit 106 repeats communication of a synchronization control message described above with reference to FIG. 2 and calculates the time difference between the time count control unit 106 and the time count control unit 122 a plurality of times. In step S902, based on the plurality of time differences calculated in step S901, the time count control unit 106 calculates a correction value used to correct the time managed by the time count control unit 106. As the correction value calculation method, the minimum value of the plurality of time differences, the average value of correction values, or the like can be used. In step S903, the time count control unit 106 corrects the time managed by the time count control unit 106 using the correction value calculated in step S902. In step S904, the time count control unit 106 saves the correction value used for correction in step S903 and the synchronization procedure execution interval.

Figure 10:
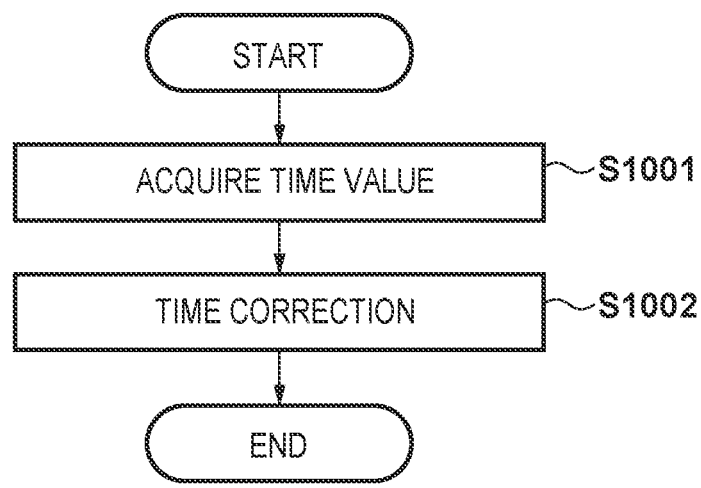
FIG. 10 shows a flowchart of time synchronization by the time count control unit 106 during imaging according to the third embodiment.

FIG. 10 shows a flowchart of time synchronization by the time count control unit 106 during imaging according to this embodiment. This procedure is executed at the synchronization procedure execution interval (for example, once a sec) saved by the time count control unit 106 in step S903 of FIG. 9. In step S1001, the time count control unit 106 acquires the saved correction value. In step S1002, the time count control unit 106 corrects the time managed by the time count control unit 106 using the correction value acquired in step S1001.

Time correction processing according to this embodiment will be described next with reference to FIG. 11. FIG. 11 is a view showing the procedure of time correction processing according to this embodiment. The time count control unit 106 in the radiation imaging apparatus 101 and the time count control unit 122 in the irradiation control apparatus 120 perform a time count operation from the starting point set to activation of a radiation imaging system 100. Before imaging is started, the time synchronization processing of the time count control unit 106 and the time count control unit 122 is executed as described with reference to FIG. 2.

When an exposure button 115 is pressed (ON state) by an operator, the time count control unit 122 in the irradiation control apparatus 120 acquires a time value "10050" that is the current time. The time count control unit 122 sets a time obtained by adding a predetermined time to the current time as an expected irradiation start time to start exposure (irradiation). Here, the predetermined time is a time that is long enough to perform message exchange between the radiation imaging apparatus 101 and the irradiation control apparatus 120 and shift to an imaging preparation operation of radiation detection by the radiation imaging apparatus 101. In addition, the predetermined time is preferably a time that does not make the operator unnecessarily wait and lower the operability. In addition, the predetermined time may be calculated in advance and set at the time of system design or may dynamically be decided by the pre-negotiation by the communication between the irradiation control apparatus 120 and the radiation imaging apparatus 101. In the example shown in FIG. 11, the predetermined time has a time value "100", and an expected irradiation start time "10150" is calculated.

After the expected irradiation start time is calculated, the irradiation control apparatus 120 transmits an imaging request message (message representing an imaging start) 1100 including the expected irradiation start time as a parameter to the radiation imaging apparatus 101. Note that the irradiation control apparatus 120 may include information (parameters) corresponding to the radiation irradiation time length (the length and irradiation window of a radiation pulse and the like) and an irradiation cycle (a frame rate and the like) into the imaging request message 1100. In addition, these parameters need not always be included in the imaging request message 1100 and may be set or transmitted in advance by another means before imaging, as described above. Furthermore, another parameter that is not explicitly described here may be included in the imaging request message 1100 and transmitted.

Upon receiving the imaging request message 1100, the time count control unit 106 in the radiation imaging apparatus 101 acquires the time of reception of the message. The time count control unit 106 compares the acquired time with the expected irradiation start time included in the received imaging request message 1100 and determines, based on an imaging mode to perform imaging, whether the imaging preparation operation (or the radiation detection operation) can be completed at the expected irradiation start time. Upon determining that the imaging preparation operation can be completed, the radiation imaging apparatus 101 returns an imaging permission message 1101 to permit the irradiation control apparatus 120 to do imaging (or radiation irradiation). At the same time, the radiation imaging apparatus 101 plans the imaging preparation operation. As described above, upon receiving irradiation information concerning the irradiation time to start radiation irradiation, the driving control unit 105 in the radiation imaging apparatus 101 controls, based on the irradiation information (notified irradiation start time), to set the detection unit 107 in a state capable of detecting radiation at the irradiation time. In addition, the radiation imaging apparatus 101 transmits, to the irradiation control apparatus 120, the imaging permission message 1101 representing that the detection unit 107 is set in the state capable of detecting radiation at the irradiation time.

The irradiation control apparatus 120 controls such that a radiation generation apparatus 110 emits radiation in a case in which the imaging permission information is received a predetermined time before the irradiation time (before the notified irradiation start time). For example, if the imaging permission message 1101 is received before the time indicated by the time count control unit 122 reaches the expected irradiation start time, the irradiation control apparatus 120 starts generating a timing pulse of radiation irradiation from the expected irradiation start time. Then, the irradiation control apparatus 120 plans the radiation irradiation operation based on the time of the time count control unit 122 such that a predetermined radiation pulse length and frame rate are obtained, and an irradiation pulse generation unit 123 generates the timing pulse of radiation irradiation.

On the other hand, in the radiation imaging apparatus 101 that has completed the imaging preparation operation, when the time indicated by the time count control unit 106 reaches the expected irradiation start time, the driving control unit 105 sets the operation of the detection unit 107 in an accumulation state to prepare for radiation irradiation. After the elapse of a time corresponding to the length of the radiation pulse from the accumulation state (in FIG. 11, after the time value indicated by the time count control unit 106 reaches 10150), the detection unit 107 is controlled to a charge readout state, and a radiation image is acquired. FIG. 11 shows a driving control signal representing the driving (charge readout) timing to the detection unit 107.

After that, like the irradiation control apparatus 120, the radiation imaging apparatus 101 plans the imaging operation (the accumulation operation, the readout operation, and the like) based on the time of the time count control unit 106 such that a predetermined frame rate is obtained, and an imaging control unit 102 executes the imaging operation. During continuation of the imaging operation, the radiation imaging apparatus 101 continuously periodically transmits a normal message 1102 (broken arrows in FIG. 11) to the irradiation control apparatus 120. During reception of the normal message 1102, the irradiation control apparatus 120 determines that the radiation imaging apparatus 101 is normally continuing the operation.

During capturing of a moving image, since time synchronization by time synchronization message exchange shown in FIG. 9 is not executed, a deviation is assumed to occur between the times managed by the time count control unit 122 and the time count control unit 106. FIG. 11 shows an example in which when time synchronization is executed at time 10000 by the time count control unit 106 and the time count control unit 122 before the imaging start, the time synchronization shown in FIG. 11 is executed at a time interval of 1000. When the time value indicated by the time count control unit 106 reaches 11000, the time managed by itself is corrected using the correction value calculated and saved in advance by the time count control unit 106. In this example, since the time synchronization correction value is "−5", the time count control unit 106 performs correction such that the time value changes from 11000 to 10995. By performing this correction, the time count control unit 106 can synchronize the time with the time count control unit 122.

As described above, according to this embodiment, even in a case in which congestion occurs on a communication line during moving image output or the like, and the correction value for time synchronization by time synchronization message communication cannot correctly be calculated, the time count control unit 106 corrects the time managed by itself based on a correction value acquired in advance. Accordingly, the time count control unit 106 can synchronize the time with the time count control unit 122, and correct radiation irradiation can be performed even in a case of signal delay.

Note that the correction using the correction value need not always be performed during capturing of a moving image (during image output). For example, correction may be done when the time error exceeds a threshold. As the threshold of the time error, the range of fluctuation of the round trip time is preferably set to 1 msec based on the network use amount of moving image data transfer.

Additionally, in this embodiment, time synchronization message communication is performed to calculate the time synchronization correction value except during image output. However, for example, time correction value information may be calculated at a timing to update the following fixed dark data. If the clock of the radiation imaging apparatus has a conspicuous deviation due to a temperature fluctuation, the temperature during updating of the fixed dark data to drive the detection unit 107 and the temperature during capturing of a moving image are assumed to equal. Hence, the clock of the radiation imaging apparatus may be corrected during capturing of a moving image based on the time synchronization correction value during updating of the fixed dark data. The fixed dark data is correction image data obtained in a radiation non-exposure state and used to correct a captured radiation image. The fixed dark data is image data fixed until it is updated at a predetermined timing.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-025354, filed Feb. 15, 2018, which is hereby incorporated by reference herein in its entirety.

What is claimed is:

1. A radiation imaging apparatus, comprising:
   an acquisition unit configured to acquire image data by detecting radiation emitted by a radiation generation apparatus;
   a time count control unit configured to manage a first time in the radiation imaging apparatus;
   a generation unit configured to generate a synchronization control message to be transmitted to synchronize a second time managed by an irradiation control apparatus configured to control radiation irradiation by the radiation generation apparatus with the first time managed by the time count control unit; and a transmission unit configured to transmit the image data and the synchronization control message, wherein the transmission unit transmits the synchronization control message with priority over the image data when timings of transmission of the synchronization control message and the image data overlap.

2. A radiation imaging apparatus, comprising:

an acquisition unit configured to acquire image data by detecting radiation emitted by a radiation generation apparatus;

a time count control unit configured to manage a first time in the radiation imaging apparatus;

a generation unit configured to generate a synchronization control message to be transmitted to synchronize a second time managed by an irradiation control apparatus configured to control radiation irradiation by the radiation generation apparatus with the first time managed by the time count control unit;

a transmission unit configured to transmit the image data and the synchronization control message; and a buffer configured to store the image data and the synchronization control message and output the image data and the synchronization control message to the transmission unit, wherein the transmission unit transmits the synchronization control message with priority over the image data, the buffer outputs the synchronization control message to the transmission unit with priority over the image data, and the transmission unit transmits one of the image data and the synchronization control message in an order of input from the buffer.

3. The apparatus according to claim 2, further comprising an order control unit configured to control, for the buffer, an order of output of the image data and the synchronization control message to the transmission unit.

4. The apparatus according to claim 3, wherein the order control unit controls the order of output to output the synchronization control message to the transmission unit before the image data if the synchronization control message is stored in the buffer in a state in which the image data is stored in the buffer.

5. A radiation imaging apparatus, comprising:

an acquisition unit configured to acquire image data by detecting radiation emitted by a radiation generation apparatus;

a time count control unit configured to manage a first time in the radiation imaging apparatus;

a generation unit configured to generate a synchronization control message to be transmitted to synchronize a second time managed by an irradiation control apparatus configured to control radiation irradiation by the radiation generation apparatus with the first time managed by the time count control unit;

a transmission unit configured to transmit the image data and the synchronization control message; and a first buffer configured to store the image data, a second buffer configured to store the synchronization control message, and a selection unit configured to select and output to the transmission unit one of the image data output from the first buffer and the synchronization control message output from the second buffer, wherein the transmission unit transmits the synchronization control message with priority over the image data, the selection unit selects and outputs the synchronization control message to the transmission unit with priority over the image data, and the transmission unit transmits one of the image data and the synchronization control message in an order of input from the first buffer or the second buffer.

6. The apparatus according to claim 5, wherein the selection unit selects and outputs the synchronization control message to the transmission unit before the image data if the synchronization control message is stored in the second buffer in a state in which the image data is stored in the first buffer.

7. A method of controlling a radiation imaging apparatus, comprising the steps of:

acquiring image data by detecting radiation emitted by a radiation generation apparatus;

generating a synchronization control message to be transmitted to synchronize a time managed by an irradiation control apparatus configured to control radiation irradiation by the radiation generation apparatus with a time in the radiation imaging apparatus; and transmitting the image data and the synchronization control message, wherein in the transmitting, the synchronization control message is transmitted with priority over the image data when timings of transmission of the synchronization control message and the image data overlap.

8. A non-transitory computer-readable storage medium storing a computer program for controlling a computer to execute a method of controlling a radiation imaging apparatus, the method comprising the steps of:

acquiring image data by detecting radiation emitted by a radiation generation apparatus;

generating a synchronization control message to be transmitted to synchronize a time managed by an irradiation control apparatus configured to control radiation irradiation by the radiation generation apparatus with a time in the radiation imaging apparatus; and transmitting the image data and the synchronization control message, wherein in the transmitting, the synchronization control message is transmitted with priority over the image data when timings of transmission of the synchronization control message and the image data overlap.

9. A radiation imaging system, comprising:

a first acquisition unit configured to acquire a first time managed by an irradiation control apparatus configured to control radiation irradiation by a radiation generation apparatus;

a second acquisition unit configured to acquire a second time managed by a radiation imaging apparatus configured to acquire image data by detecting radiation emitted by the radiation generation apparatus;

a calculation unit configured to calculate a correction value based on a plurality of time differences between the first and the second time which are obtained by repeating a communication of a synchronization control message between the radiation generation apparatus and the radiation imaging apparatus at a predetermined interval during a time when the radiation imaging apparatus is not acquiring the image data; and a correction unit configured to correct the second time using the correction value calculated by the calculation unit.

10. The system according to claim 9, wherein the correction unit corrects the second time using the correction value at the predetermined interval during a time when the radiation imaging apparatus is acquiring the image data.

11. The system according to claim 9, wherein the correction unit corrects the second time using the correction value in a case in which the correction value exceeds a predetermined threshold during a time when the radiation imaging apparatus is acquiring the image data.

12. The system according to claim 9, further comprising a control unit configured to control detection of radiation by the radiation imaging apparatus, wherein the control unit controls the radiation imaging apparatus to detect the radiation emitted by the radiation generation apparatus and acquire the image data when the second time reaches an expected irradiation start time transmitted from the irradiation control apparatus.

* * * * *